US00PP10413P

United States Patent [19]

Alston

[11] Patent Number: Plant 10,413

[45] Date of Patent: May 26, 1998

[54] MANDEVILLA PLANT NAMED 'PSJAM DP1'

[75] Inventor: Jimmy A. Alston, Hodges, S.C.

[73] Assignee: Geo. W. Park Seed Co., Inc., Greenwood, S.C.

[21] Appl. No.: 717,869

[22] Filed: Sep. 23, 1996

[51] Int. Cl.[6] ..... A01H 5/00

[52] U.S. Cl. ..... Plt./54.1

[58] Field of Search ..... Plt./54.1

[56] References Cited

U.S. PATENT DOCUMENTS

P.P. 8,842 7/1994 Henny ..... Plt./54.1
P.P. 9,118 4/1995 Petersen ..... Plt./54.1

*Primary Examiner*—James R. Feyrer
*Assistant Examiner*—Kent L. Bell
*Attorney, Agent, or Firm*—Foley & Lardner

[57] ABSTRACT

A new and distinct Mandevilla plant named 'PSJAM DP1', characterized particularly by its deep pink flower color, large flower size, wide overlapping corolla lobes, floriferous habit, and its ease of propagation.

3 Drawing Sheets

The present invention comprises a new and distinct cultivar of Mandevilla plant, hereinafter referred to by the cultivar name 'PSJAM DP1'.

'PSJAM DP1' originated from a self-pollination of Mandevilla 'Alice Du Pont'. Mandevilla 'Alice Du Pont' represents the backcross of *M.×amabilis×M. splendens* where *M.×amabilis* is an interspecific hybrid of *M. splendens×* an unknown species of Mandevilla, according to *Hortus Third* (Bailey 1976).

The self-pollinations were made by the inventor on a single plant being grown at Hodges, S.C. during the summer of 1993. 'PSJAM DP1' was discovered and selected as one flowering plant within the progeny of the stated parentage by the inventor in April 1994, in greenhouses in Greenwood, S.C.

Asexual propagation of the new cultivar by cuttings as performed by the inventor in July 1994, in Greenwood, S.C., showed the first generation to be true to type. Successive generations of asexual propagation have demonstrated that the combination of characteristics as herein disclosed for 'PSJAM DP1' are firmly fixed and can be successively reproduced asexually.

'PSJAM DP1' has not been observed under all possible environmental conditions. The phenotype may vary significantly with variations in the environment such as temperature, light intensity and day length, without, however, any variation in genotype. The following observations, measurements and comparisons describe plants grown in Greenwood S.C., under greenhouse conditions which approximate those generally used in commercial practice.

The following traits have been repeatedly and consistently observed and are determined to be basic characteristics of 'PSJAM DP1' which in combination distinguish this Mandevilla as a new and distinct cultivar:

(1) The flowers are large, deep pink in color and funnel-form in shape. Flower color darkens significantly after flowers have been open 1–2 days, and the flowers remain on the plant an additional 3–4 days. The lobe sutures within the flower throat are yellow and the areas between the sutures are yellow overlayed with pink.

(2) The corolla lobes are wide and overlapping. They are oblique obovate with an off-center abrupt acuminate apex. The corolla lobe margins are slightly undulate and most are slightly picoteed a light pink.

(3) The cultivar is highly floriferous with each penduncle producing in excess of 40 individual flowers and having up to 4 flowers open on the same day.

(4) Under greenhouse conditions, the cultivar blooms year round but is in heavy bloom from April through October.

(5) The leaves are oblong to elliptic with an abrupt acuminate point. They are leathery, polished and dark green in color, and the cultivar is evergreen.

In comparison to the parent 'Alice DuPont', the new cultivar has a darker pink flower color, wider corolla lobes that overlap, and a larger corolla diameter. In comparison to the cultivar 'Ruby Star', disclosed in U.S. Plant Pat. No. 8,842, the new cultivar has a deep pink rather than red flower color, has wider corolla lobes that overlap more, and a larger corolla diameter.

The accompanying color photographic drawings show typical inflorescence and foliage characteristics of 'PSJAM DP1', with the colors being as accurate as possible with illustrations of this type.

The photograph on sheet is a perspective view of the plant.

The photograph on sheet 2 is a photo of a single inflorescence.

The photograph on sheet 3 is a comparative presentation of flowers of 'Alice du Pont' (lower right), 'PSJAM DP1' (at top) and 'Ruby Star' (lower left).

In the following description, color references are made to The Royal Horticultural Colour Chart (R.H.S.) The color values were determined on Jul. 12 and Jul. 15, 1996, between 2:00 and 3:00 p.m. in a greenhouse in Greenwood, S.C., under 6000 foot candles of light intensity.

Classification:

A. *Botanical.*—Progeny from selfing the backcross of *M.×amabilis×M. splendens.*

B. *Commercial.*—Mandevilla.

Description

A. Plant:

*Habit.*—Twining vine; twining counter-clockwise; evergreen.

*Height.*—Has not been observed under conditions conducive to maximum growth but has reached 9 m in the greenhouse.

*Stem color.*—Immature, 144B; mature, 152B.

*Stem texture.*—Pubescent.

*Internode length.*—5–25 cm, with the basal ones being the shortest.

*Nodal appendages.*—3–5 Parted dentate; normally 5; color 144A.

B. Foliage:

*Arrangement.*—Opposite.

*Shape.*—Oblong to elliptic with an abrupt acuminate point and cordate base; dimensions vary from 6–11 cm wide and 10–17 cm long.

*Margin.*—Entire.

*Texture.*—Glabrescent and slightly undulated.

*Color.*—Top of immature leaf, 143A; top of mature leaf, 137A; bottom of immature leaf, 143D; bottom of mature leaf, 138B; the mid-rib for both immature and mature leaves is 143C; the petioles of both immature and mature leaves are 144B.

C. Inflorescence:

*Type.*—Racemose; in excess of 40 blooms over its life.

*Peduncle.*—60 cm with flower buds still being produced, color 144B.

*Pedicels.*—1.5–2 cm long, twisted; color 144C, turning to 178C after corolla drop.

*Bracts.*—0.6–0.7 cm long, triangular shaped; the basal color is 144B; the tip color is 178C.

*Sepals.*—5 in number, each 0.8–1.1 cm long and 0.3-14 0.4 wide at the base; exterior color is 144B, interior color is 144D; the tips are 178C.

*Corolla type.*—Funnelform; lobes 5; the lobes are oblique obovate with an off-center abrupt acuminate apex.

*Corolla size* (6 *days old*).—tube is 0.4 cm in diameter and 1.4–1.6 cm long; throat is 2.8–3.2 cm long, conical, and the opening is 2.4–2.6 cm; the lobes are 5.2–6.3 cm long and 5.2–6.5 cm wide; overall face of corolla is 11–14 cm.

*Corolla color* (*in bud*).—The basal tube is 145B, with a shading of 179B; the tube color runs into the throat which is 151B; the lobes still in the roll are 52D on the narrow side; as the bud starts to unfold the wide sides of the lobes are 142D with a very distinct line of demarcation between the two sides possibly influenced by the light intensity.

*Corolla color* (2 *days old*).—Exterior: the tube is 145B; the junction of the tube and throat is 145D; the throat is 53D; the narrow sides of lobes are 53D and the wide sides 65D. Interior: the color deep in the throat is 9B, transitioning through 21B to 65D at the junction of the throat and lobes; the yellow color (9B) follows the lobe sutures up the throat to a spot of 155C at the point of separation of the lobes; the narrow sides of the lobes under the overlap of the adjoining lobes are 58D; the wide sides of the lobes are 58B; the picoteed area is 65D.

*Corolla color* (5 *days old*).—Exterior: The tube is 145D; the junction of the tube and throat is 155C; the throat is 53D; the narrow sides of the lobes are 53D, and the wide sides are 52B. Interior: The color deep in the throat is 9B, transitioning through 21C to 65B at the junction of the throat and lobes; the yellow color (9B) follows the lobe sutures up the throat half way to the point of separation of the lobes; the narrow sides of the lobes under the overlap of the adjoining lobe are 52C, and the wide sides 52A; the picoteed area is 65B.

D. Fruit: No fruit has been observed on the new cultivar.

E. Cold hardiness: The coltivar has not been observed in the situations to evaluate its hardiness.

I claim:

1. A new and distinct Mandevilla plant named 'PSJAM DP1, 'as illustrated and described.

* * * * *

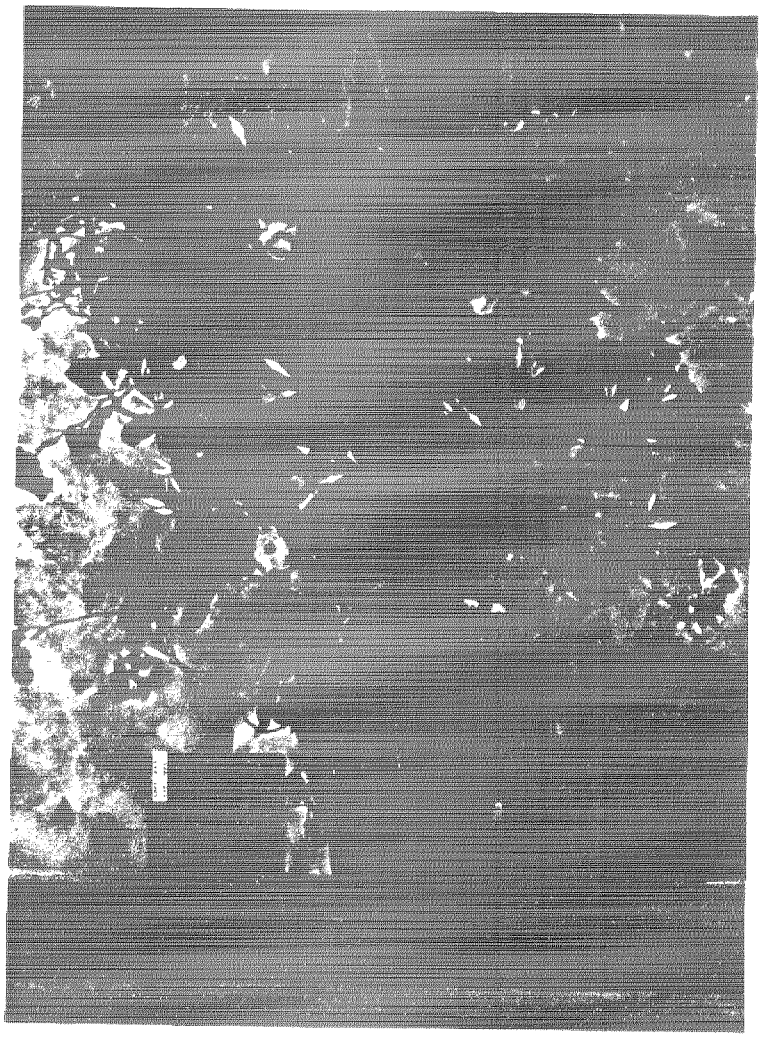

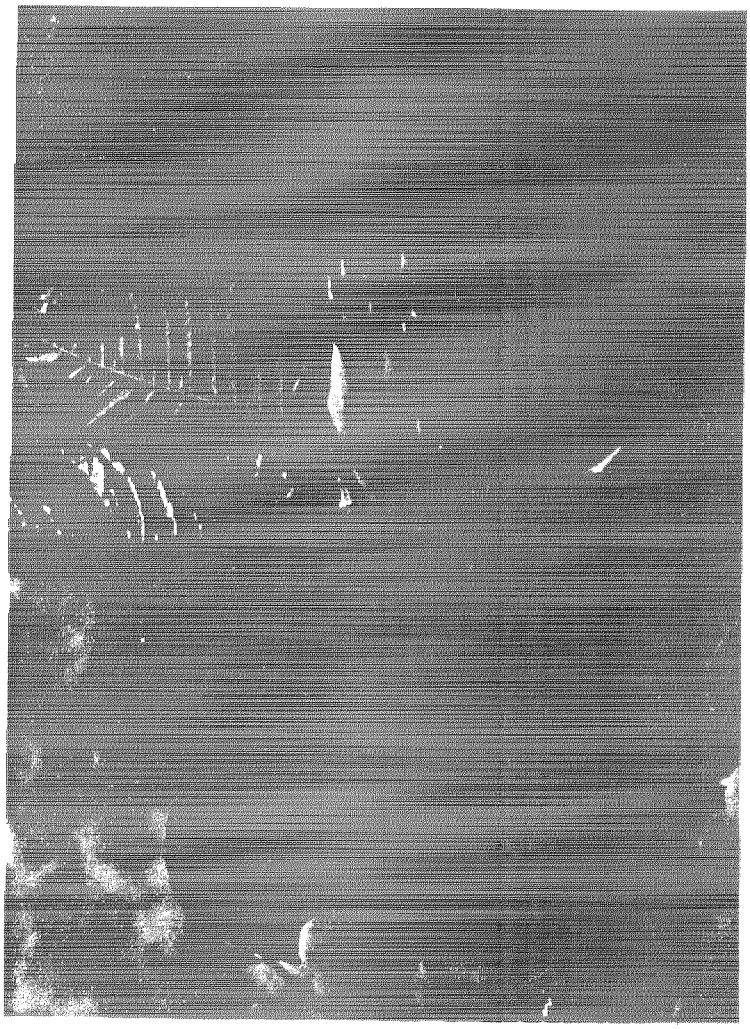

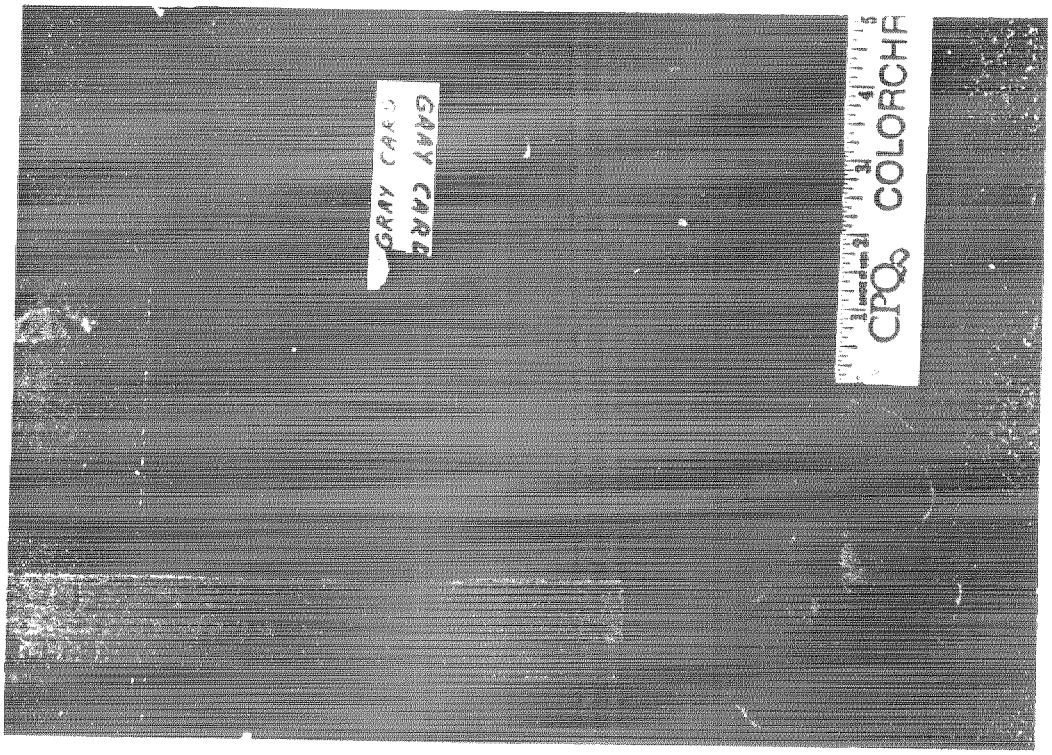

PLT-232 SR
C5203 OR PP 010,413